United States Patent

Dhingra et al.

[11] Patent Number: 5,811,420
[45] Date of Patent: Sep. 22, 1998

[54] FUNGARRESTINS

[75] Inventors: Urvashi Hooda Dhingra, Nutley, N.J.; Haruyoshi Shirai, Kanagawa-ken; Yuki Takehana, Fujisawa, both of Japan; Peter Michael Wovkulich, Nutley, N.J.; Nami Yabuki, Chigasaki, Japan

[73] Assignee: Hoffmann-La Roche Inc., Nutley, N.J.

[21] Appl. No.: 870,798

[22] Filed: Jun. 6, 1997

[30] Foreign Application Priority Data

Jun. 7, 1996 [EP] European Pat. Off. .............. 96109115

[51] Int. Cl.$^6$ ........................ A61K 31/55; A61K 31/335; C07D 267/02; C07D 323/00
[52] U.S. Cl. ........................... 514/211; 514/450; 540/488; 540/547; 549/267; 549/349
[58] Field of Search ..................... 549/267, 349; 514/450, 211; 540/488, 547

[56] References Cited

U.S. PATENT DOCUMENTS 5,317,101 5/1994 Oldfield et al. .......................... 540/488
5,350,763 9/1994 Feighner et al. ........................ 514/450

FOREIGN PATENT DOCUMENTS 07069882 3/1995 Japan .
95/10514 4/1995 WIPO .

Primary Examiner—Mukund J. Shah
Assistant Examiner—Bruck Kifle
Attorney, Agent, or Firm—George W. Johnston; Dennis P. Tramaloni; Alan P. Kass

[57] ABSTRACT

Compounds of formula (I),

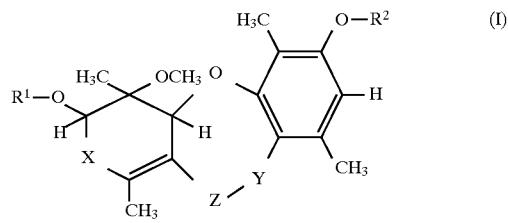

wherein $R^1$ and $R^2$ are independently hydrogen, unsubstituted lower alkyl or lower alkyl substituted by lower alkoxy or lower alkyl thio, or acyl which is unsubstituted or substituted by one or more of lower alkyl, lower alkyl substituted by halogen, and lower alkoxy;

X is CO or CHOH;

Y is CO or $CH_2$; and

Z is O or NH, and epimers and enantiomers thereof, or the physiologically usable salts thereof are useful as anti-tumor agents. They can be prepared by fermentation of *Aspergillus sp.* and, optionally, subsequent modification of functional groups.

29 Claims, No Drawings

FUNGARRESTINS

The present invention relates to compounds of formula (I),

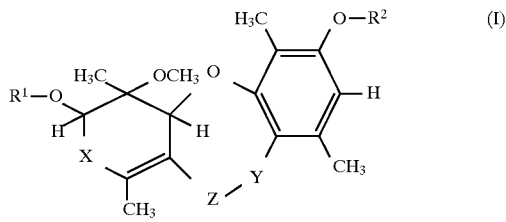

wherein
- $R^1$ and $R^2$ are independently hydrogen, unsubstituted lower alkyl, lower alkyl substituted by lower alkoxy or lower alkyl thio, or acyl which is unsubstituted or substituted by one or more of lower alkyl, lower alkoxy, lower alkyl substituted by hydrogen or halogen or;
- X is CO or CHOH;
- Y is CO or $CH_2$; and
- Z is O or NH, and epimers or enantiomers thereof, or the physiologically usable salts thereof.

As used herein, the term "lower alkyl" refers to hydrocarbon groups containing up to and including 6, preferably 1–2, carbon atoms unless otherwise specified which can be unsubstituted or substituted by lower alkoxy or lower alkyl thio. Thus, for example, "lower alkyl" is for example, methyl, ethyl, t-butyl, n-pentyl, substituted methyl such as methoxymethyl, methylthiomethyl.

"Acyl" can be aliphatic, araliphatic or aromatic acyl. Preferably, aliphatic acyl has 1 to 6 carbon atom(s) such as formyl, acetyl, propionyl, n-butyryl, iso-butyryl, and pivaloyl. Araliphatic acyl is, for example, phenylacetyl which can be substituted by one or more substitutents such as lower alkoxy and lower alkyl substituted by halogen for example, α-Methoxy-α-(trifluoromethyl)-phenylacetyl. Preferably, aromatic acyl is benzoyl which may be unsubstituted or substituted with lower alkyl such as, for example, methyl, ethyl, t-butyl, and n-pentyl or with halogen such as fluorine, chlorine, bromine, or iodine. Preferably, X is CO, Y is CO and Z is O.

The present invention is also concerned with compositions containing one or more compounds as defined in the above formula (I) or physiologically usable salts thereof; and the use of these compounds or physiologically usable salts thereof as antitumor agents; a process for producing these compounds or physiologically usable salts thereof, and microorganisms capable of producing certain of these compounds.

More particularly this invention is concerned with compounds identified as compound A, A-1, A-2, A-3, A-4, A-5, A-6, A-7, A-8, A-9, and A-10, and their respective epimers compounds B, B-1, B-2, B-3, B-4, B-5 and B-6 of the formula (I) as defined below:

Compound A: I, $R^1$=H, $R^2$=H, X=CO, Y=CO, Z=O (3,7-dihydroxy-6-methoxy-1,4,6,9-tetramethyl-6,7-dihydro-5aH-dibenzo[b,e][1,4]dioxepine-8,11 -dione);

1) Appearance: white crystals 2) Melting point: 187°–188° C. 3) Specific rotation: $[\alpha]^{23}_D$=+272° (c=0.56, in methanol) 4) Molecular weight (FAB-MS method) Negative ion mode: m/z 347 (M–H)⁻ 5) Molecular formula: $C_{18}H_{20}O_7$ 6) High resolution mass spectroscopy (for M–H): Found: 347.1146 Calcd. for $C_{18}H_{19}O_7$: 347.1131 7) UV λmax nm (ε): in MeOH: 213 (20,100), 282 (14,500) in MeOH+N/10 HCl: 215 (18,400), 278 (14,200) in MeOH+N/10 NaOH: 248 (16,100), 297 (13,900) 328 (17,000) 8) IR spectrum: in KBr tablet, Main absorption wavenumbers (cm–1) are as follows: 3410, 2932, 1729, 1678, 1639, 1604, 1232, 1126 9) ¹H-NMR spectrum: 400 MHz, in DMSO-$d_6$ used TMS as an internal standard δ: 1.01 (3H, s), 1.77 (3H, d, J=2Hz), 2.09 (3H, s), 2.38 (3H, s), 3.28 (3H, s), 4.32 (1H, d J=5Hz), 5.35 (1H, q, J=2Hz) 5.52 (1H, d, J=5Hz, $D_2O$ exchangeable), 6.62 (1H, s), 10.60 (1H, s, $D_2O$ exchangeable) 10) ¹³C-NMR spectrum: 100 MHz, in DMSO-$d_6$ used TMS as an internal standard δ: 8.3, 8.4, 13.3, 21.8, 50.1, 74.6, 80.2, 82.8, 110.8, 113.7, 114.6, 117.1, 142.1, 159.2, 160.2, 160.8, 161.1, 197.5 11) Solubility: Soluble: dimethyl sulfoxide, ethyl acetate, methanol Insoluble: n-hexane, water Compound A-1: 1, $R^1$=acetyl, $R^2$=acetyl, X=CO, Y=CO, Z=O (3,7-di(methylcarbonyloxy)-6-methoxy-1,4,6,9-tetramethyl-6,7-dihydro-5aH-dibenzo[b,e][1,4] dioxepine-8,11-dione);

1) Appearance: white powder 2) Molecular weight (FAB-MS method) Positive ion mode: m/z 433 (M+H)⁺ 3) Molecular formula: $C_{22}H_{24}O_9$ 4) ¹H-NMR spectrum: 400 MHz, in DMSO-$d_6$ used TMS as an internal standard δ: 1.09 (3H, s), 1.80 (3H, d, J=2Hz), 2.10 (3H, s), 2.17 (3H, s), 2.34 (3H, s), 2.45 (3H, s), 3.23 (3H, s), 5.69 (1H, s), 5.78 (1H, q, J=2Hz), 7.04 (1H, s)

Compound A-2: $R^1$=H, $R^2$=p-bromobenzoyl, X=CO, Y=CO, Z=O (3-(4-bromobenzoyl)-7-hydroxy-6-methoxy-1,4,6,9-tetramethyl-6,7-dihydro-5aH-dibenzo[b,e][1,4]dioxepine-8,11-dione);

1) Appearance: white powder 2) Molecular weight (FAB-MS method) Positive ion mode: m/z 531 (M+H)⁺ 3) Molecular formula: $C_{25}H_{23}BrO_8$ 4) ¹H-NMR spectrum: 400 MHz, in DMSO-$d_6$ used TMS as an internal standard: δ: 1.00 (3H, s), 1.80 (3H, d, J=2Hz), 2.14 (3H, s), 2.45 (3H, s), 3.31 (3H, s), 4.29 (1H, s), 5.56 (1H, d, J=2Hz), 5.71 (1H, broad s), 7.17 (1H, s), 7.85 (2H, d, J=8.5Hz), 8.08 (2H, d, J=8.5Hz)

Compound A-3: I, $R^1$=p-bromobenzoyl, $R^2$=p-bromobenzoyl, X=CO, Y=CO, Z=O (3,7-di(4-bromobenzoyl)-6-methoxy-1,4,6,9-tetramethyl-6,7-dihydro-5aH-dibenzo[b,e][1,4]dioxepine-8,11-dione);

1) Appearance: white powder 2) Molecular weight (FAB-MS method) Positive ion mode : m/z 713 (M+H)⁺ 3) Molecular formula: $C_{32}H_{26}Br_2O_9$ 4) ¹H-NMR spectrum: 400 MHz, in $CDCl_3$ used TMS as an internal standard δ: 1.44 (3H, s), 1.97 (3H, d, J=2Hz), 2.19 (3H, s), 2.57 (3H, s), 3.38 (3H, s), 5.21 (1H, d, J=2Hz), 5.73 (1H, s), 6.97 (1H, s), 7.62 (2H, d, J=8.5Hz), 7.69 (2H, d, J=8.5Hz), 7.95 (2H, d, J=9Hz), 8.05 (2H, d, J=9Hz)

Compound A-4: I, $R^1$=H, $R^2$=$CH_3$, X=CO, Y=CO, Z=O ((5aS,6S,7S)-7-hydroxy-3,6-dimethoxy-1,4,6,9-tetramethyl-6,7-dihydro-5aH-dibenzo[b,e]p1,4]dioxepine-8,11-dione);

1) Appearance: white powder 2) Molecular weight (EI-MS method) Positive ion mode: m/z 362 (M)⁺˙ 3) Molecular formula: $C_{19}H_{22}O_7$ 4) ¹H-NMR spectrum: 270 MHz, in $CDCl_3$ used TMS as an internal standard δ: 1.20 (3H, s), 1.97 (3H, d, J=2Hz), 2.20 (3H, s), 2.56 (3H, s), 3.50 (3H, s), 3.81 (1H, d, J=2.5Hz), 3.89 (3H, s), 4.22 (1H, d, J=2.5Hz), 4.91 (1H, q, J=2Hz), 6.60 (1H, s)

Compound A-5: 1, $R^1$=(–)-α-methoxy-α-(trifluoromethyl)phenylacetyl, $R^2$=$CH_3$, X=CO, Y=CO, Z=O ((S)-3,3,3-trifluoro-2-methoxy-2-phenyl-propionic acid (5aS,6R,7 R)-2,6-dimethoxy-1,4,6,9-tetramethyl-8-11-dioxo-5a,6,7,8-tetrahydro-11H-dibenzo[b,e][1,4]dioxepin-7-yl ester);

1) Appearance: white powder 2) Molecular weight (FAB-MS method) Positive ion mode : m/z 579 (M+H)⁺ 3)

Molecular formula: $C_{29}H_{29}F_3O_9$ 4) $^1$H-NMR spectrum: 400 MHz, in CDCl$_3$ used TMS as an internal standard 67 : 1.29 (3H, s), 1.97 (3H, d, J=2Hz), 2.13 (3H, s), 2.57 (3H, s), 3.09 (3H, s), 3.72 (3H, d, J=1Hz), 3.89 (3H, s), 4.98 (1H, d, J=2Hz), 5.60 (1H, s), 6.61 (1H, s), 7.42 (3H, m), 7.74 (2H, m)

Compound A-6: I, R$^1$=(+)-α-methoxy-α-(trifluoromethyl)phenylacetyl, R$^2$=CH$_3$, X=CO, Y=CO, Z=O ((R)-3,3,3-trifluoro-2-methoxy-2-phenyl-propionic acid (5aS,6R,7S)-2,6-dimethoxy-1,4,6,9-tetramethyl-8,11-dioxo-5a,6,7,8-tetrahydro-11H-dibenzo[b,e][1,4]dioxepin-7-yl ester);

1) Appearance: white powder 2) Molecular weight (FAB-MS method) Positive ion mode: m/z 579 (M+H)$^+$ 3) Molecular formula: $C_{29}H_{29}F_3O_9$ 4) $^1$H-NMR spectrum: 400 MHz, in CDCl$_3$ used TMS as an internal standard 67 : 1.38 (3H, s), 1.96 (3H, d, J=2Hz), 2.20 (3H, s), 2.58 (3H, s), 3.33 (3H, s), 3.63 (3H, d, J=1Hz), 3.91 (3H, s), 5.07 (1H, d, J=2Hz), 5.66 (1H, s), 6.62 (1H, s), 7.44 (3H, m), 7.70 (2H, m)

Compound A-7: I, R$^1$=CH$_2$SCH$_3$, R$^2$=CH$_3$, X=CO, Y=CO, Z=O ((5aS,6R,7S)-3,6-dimethoxy-1,4,6,9-tetramethyl-7-methylsulfanylmethoxy-6,7-dihydro-5aH-dibenzo[b,e][1,4]dioxepine-8,11-dione);

1) Appearance: white powder 2) Molecular weight (FAB-MS method) Positive ion mode: m/z 423 (M+H)$^+$ 3) Molecular formula: $C_{21}H_{26}O_7S$ 4) $^1$H-NMR spectrum: 500 MHz, in CDCl$_3$ used TMS as an internal standard δ: 1.40 (3H, s), 1.88 (3H, d, J=1.5Hz), 2.16 (3H, s), 2.18 (3H, s), 2.53 (3H, s), 3.43 (3H, s), 3.88 (3H, s), 4.29 (1H, s), 4.86 (2H, d, J=12.5Hz), 4.93 (1H, q, J=1.5Hz), 6.55 (1H, s)

Compound A-8: 1, R$^1$=H, R$^2$=H, X=CHOH, Y=CO, Z=O (3,7,8-trihydroxy-6-methoxy-1,4,6,9-tetramethyl-6,7-dihydro-5aH-dibenzo[b,e][1,4]dioxepine-11-one);

1) Appearance: white powder 2) Molecular weight (EI-MS method) Positive ion mode: m/z 350 (M)$^{+\cdot}$ 3) Molecular formula: $C_{18}H_{22}O_7$ 4) $^1$H-NMR spectrum: 500 MHz, in DMSO-d$_6$ used TMS as an internal standard δ: 1.43 (3H, s), 1.63 (3H, s), 2.01 (3H, s), 2.21 (3H, s), 3.28 (3H, s), 3.56 (1H, d, J=5, 4.5Hz), 4.07 (1H, ddd, J=8, 4.5, 1Hz), 4.59 (1H, d, J=5Hz, D$_2$O exchangeable), 4.67 (1H, d, J=1Hz), 4.77 (1H, d, J=8Hz D$_2$O exchangeable), 6.40 (1H, s), 9.82 (1H, broad s, D$_2$O exchangeable)

Compound A-9: I, R$^1$=H, R$^2$=H, X=CO, Y=CH$_2$, Z=O ((5aS,6S,7S)-3,7-dihydroxy-6-methoxy-1,4,6,9-tetramethyl-6,7-dihydro-5aH,11H-dibenzo[b,e][1,4]dioxepine-8-one);

1) Appearance: white powder 2) Molecular weight (FAB-MS method) Positive ion mode: m/z 335 (M+H)$^+$ 3) Molecular formula: $C_{18}H_{22}O_6$ 4) $^1$H-NMR spectrum: 500 MHz, in DMSO-d$_6$ used TMS as an internal standard δ: 1.15 (3H, s), 1.66 (3H, s), 2.01 (3H, s), 2.12 (3H, s), 3.27 (3H, s), 4.26 (1H, d, J=5Hz), 5.18 (1H, d, J=14Hz), 5.22 (1H, d, J=5Hz, D$_2$O exchangeable), 5.23 (1H, s), 5.29 (1H, d, J=14Hz), 6.39 (1H, s), 9.33 (1H, s, D$_2$O exchangeable)

Compound A-10: I, R$^1$=H, R$^2$=H, X=CO, Y=CO, Z=NH;

1) Appearance: white powder 2) Molecular weight (FAB-MS method) Positive ion mode : m/z 348 (M+H)$^+$ 3) Molecular formula: $C_{18}H_{21}NO_6$ 4) $^1$H-NMR spectrum: 400 MHz, in MeOH-d$_4$ used TMS as an internal standard δ: 1.25 (3H, s), 1.90 (3H, d, J=1.2Hz), 2.20 (3H, s), 2.44 (3H, s), 3.36 (3H, s), 4.35 (1H, s), 4.95 (1H, broad s), 6.56 (1H, s)

Compound B: enantiomer of Compound A (3,7-dihydroxy-6-methoxy-1,4,6,9-tetramethyl-6,7-dihydro-5aH-dibenzo[b,e][1,4]dioxepine-8,11-dione);

1) Appearance: white crystals 2) Melting point: 198°–199° C. 3) Specific rotation: [α]$^{23}_D$=-8° (c=0.52, in methanol) 4) Molecular weight (FAB-MS method) Negative ion mode: m/z 347 (M-H)$^-$ 5) Molecular formula: $C_{18}H_{20}O_7$ 6) High resolution mass spectroscopy (for M-H): Found: 347.1140 Calcd. for $C_{18}H_{19}O_7$ 347.1131 7) UV λmax nm (ε): in MeOH: 220 (21,300), 290 (8,400) in MeOH+N/10 HCl: 220 (20,100), 289 (8,000) in MeOH+N/10 NaOH: 249 (17,100), 335 (12,800) 8) IR spectrum: in KBr tablet, Main absorption wavenumbers (cm$^{-1}$) are as follows: 3424, 2932, 1744, 1657, 1600, 1247, 1128 9) $^1$H-NMR spectrum: 400 MHz, in DMSO-d$_6$ used TMS as an internal standard 67 : 1.53 (3H, s), 1.66 (3H, s), 2.00 (3H, s), 2.32 (3H, s), 3.24 (3H, s), 4.27 (1H, d, J=6Hz), 5.13 (1H, s), 5.42 (1H, d, J=6Hz, D$_2$O exchangeable), 6.54 (1 H, s), 10.38 (1H, broad s, D$_2$O exchangeable) 10) $^{13}$C-NMR spectrum: 125 MHz, in DMSO-d$_6$ used TMS as an internal standard 67 : 7.7, 8.6, 15.7, 22.3, 51.3, 75.4, 77.0, 79.9, 107.9, 111.0, 113.0, 117.3, 139.7, 155.2, 155.8, 159.8, 162.2, 196.5 11) Solubility: Soluble: dimethyl sulfoxide, ethyl acetate, methanol Insoluble: n-hexane, water Compound B-1: epimer of Compound A-1 (3,7-di(methylcarbonyloxy)-6-methoxy-1,4,6,9-tetramethyl-6,7-dihydro-5aH-dibenzo[b,e][1,4]dioxepine-8,11-dione)

1) Appearance: white powder 2) Molecular weight (FAB-MS method) Positive ion mode: m/z 433 (M+H)$^+$ 3) Molecular formula: $C_{22}H_{24}O_9$ 4) $^1$H-NMR spectrum: 400 MHz, in DMSO-d$_6$ used TMS as an internal standard 67 : 1.51 (3H, s), 1.69 (3H, s), 1.98 (3H, s), 2.21 (3H, s), 2.33 (3H, s), 2.39 (3H, s), 3.28 (3H, s), 5.55 (1H, s), 5.56 (1H, s), 6.92 (1H, s)

Compound B-2: epimer of Compound A-2 (3-(4-bromobenzoyl)-7-hydroxy-6-methoxy-1,4,6,9-tetramethyl-6,7-dihydro-5aH-dibenzo[b,e][1,4]dioxepine-8,11-dione)

1) Appearance: white powder 2) Molecular weight (FAB-MS method) Positive ion mode: m/z 531 (M+H)$^+$ 3) Molecular formula: $C_{25}H_{23}BrO_8$ 4) $^1$H-NMR spectrum: 400 MHz, in DMSO-d$_6$ used TMS as an internal standard 67 : 1.55 (3H, s), 1.71 (3H, s), 2.04 (3H, s), 2.41 (3H, s), 3.26 (3H, s), 4.23 (1H, d, J=6Hz), 5.37 (1H, s) 5.46 (1H, d, J=6Hz), 7.07 (1H, s), 7.86 (2H, d, J=8Hz), 8.06 (2H, d, J=8Hz)

Compound B-3: epimer of Compound A-3

1) Appearance: white powder 2) Molecular weight (FAB-MS method) Positive ion mode: m/z 713 (M+H)$^+$ 3) Molecular formula: $C_{32}H_{26}Br_2O_9$ 4) $^1$H-NMR spectrum: 500 MHz, in CDCl$_3$ used TMS as an internal standard 67 : 1.63 (3H, s), 1.87 (3H, s), 2.13 (3H, s), 2.50 (3H, s), 3.47 (3H, s), 4.92 (1H, s), 5.95 (1H, s), 6.86 (1H, s), 7.63 (2H, d, J=9Hz), 7.69 (2H, d, J=9Hz), 7.98 (2H, d, J=8Hz), 8.06 (2H, d, J=8Hz)

Compound B-4: epimer of Compound A-4 ((5aS,6S,7R)-7-hydroxy-3,6-dimethoxy-1,4,6,9-tetramethyl-6,7-dihydro-5aH-dibenzo[b,e][1,4]dioxepine-8,11-dione)

1) Appearance: white powder 2) Molecular weight (EI-MS method) Positive ion mode: m/z 362 (M)$^{+\cdot}$ 3) Molecular formula: $C_{19}H_{22}O_7$ 4) $^1$H-NMR spectrum: 400 MHz, in CDCl$_3$ used TMS as an internal standard 67 : 1.71 (3H, s), 1.84 (3H, s), 2.08 (3H, s), 2.51 (3H, s), 3.35 (3H, s), 3.53 (1H, d, J=3.5Hz, D$_2$O exchangeable), 3.87 (3H, s), 4.43 (1H, d, J=3.5Hz), 4.76 (1H, s), 6.54 (1H, s)

Compound B-5: epimer of Compound A-5 ((S)-3,3,3-trifluoro-2-methoxy-2-phenyl-propionic acid (5aS,6R,7S)-2,6-dimethoxy-1,4,6,9-tetramethyl-8,11-dioxo-5a,6,7,8-tetrahydro-11H-dibenzo[b,e][1,4]dioxepin-7-yl ester)

1) Appearance: white powder 2) Molecular weight (FAB-MS method) Positive ion mode : m/z 579 (M+H)$^+$ 3) Molecular formula: $C_{29}H_{29}F_3O_9$ 4) $^1$H-NMR spectrum: 500 MHz, in CDCl$_3$ used TMS as an internal standard 67 : 1.61

(3H, s), 1.82 (3H, s), 2.11 (3H, s), 2.51 (3H, s), 3.30 (3H, s), 3.59 (3H, s), 3.88 (3H, s), 4.78 (1H, s), 5.81 (1H, s), 6.55 (1H, s), 7.45 (3H, m), 7.69 (2H, m)

Compound B-6: epimer of Compound A-6 ((R)-3,3,3-trifluoro-2-methoxy-2-phenyl-propionic acid (5aS,6R,7R)-2,6-dimethoxy-1,4,6,9-tetramethyl-8,11-dioxo-5a,6,7,8-tetrahydro-11H-dibenzo[b,e][1,4]dioxepin-7-yl ester)

1) Appearance: white powder 2) Molecular weight (FAB-MS method) Positive ion mode: m/z 579 (M+H)$^+$ 3) Molecular formula: $C_{29}H_{29}F_3O_9$ 4) $^1$H-NMR spectrum: 500 MHz, in $CDCl_3$ used TMS as an internal standard δ: 1.37 (3H, s), 1.83 (3H, s), 2.10 (3H, s), 2.50 (3H, s), 3.18 (3H, s), 3.72 (3H, s), 3.88 (3H, s), 4.72 (1H, s), 5.80 (1H, s), 6.55 (1H, s), 7.45 (3H, m), 7.80 (2H, m)

According to the Process provided by the present invention, Compound A ($R^1$=H, $R^2$=H, X=CO, Z=O) and its epimer Compound B ($R^1$=H, $R^2$=H, X=CO, Z=O) can be made by cultivating a microorganism belonging to the genus Aspergillus capable of producing Compounds A and/or B under aerobic condition in a culture medium and isolating Compounds A and B from the culture.

The microorganism used in the foregoing process can be used any strain (including mutants and variants) belonging to the genus Aspergillus capable of producing these compounds. Especially preferred strains are *Aspergillus japonicus* NR 7328, *Aspergillus fumigatus* NR 7329, NR 7330, NR 7331, NR 7332 and NR 7334 as well as mutants and variants thereof. *Aspergillus japonicus* NR 7328, *Aspergillus fumigatus* NR 7329, NR 7330, NR 7331, NR 7332 and NR 7334 were isolated from maize or soil samples and identified as a strain belonging to *Aspergillus japonicus* and *Aspergillus fumigatus*, respectively.

The strain denoted as *Aspergillus japonicus* NR 7328 and *Aspergillus fumigatus* NR 7329, NR 7330, NR 7331, NR 7332 and NR 7334 have been deposited with the DMS Deutsche Sammlung von Mikroorganismen und Zellkulturen GmbH, Germany, under the Budapest Treaty on May 9, 1996 as follows: *Aspergillus japonicus* NR 7328 (DSM 10677), *Aspergillus fumigatus* NR 7329 (DSM 10678), *Aspergillus fumigatus* NR 7330 (DSM 10679), *Aspergillus fumigatus* NR 7331 (DSM 10680), *Aspergillus fumigatus* NR 7332 (DSM 10681) and *Aspergillus fumigatus* NR 7334 (DSM 10682).

The cultural and morphological characteristics of *Aspergillus japonicus* NR 7328 (DSM 10677), *Aspergillus fumigatus* NR 7329 (DSM 10678), NR 7330 (DSM 10679), NR 7331 (DSM 10680), NR 7332 (DSM 10681) and NR 7334 (DSM 10682) are as follows:

Cultural Characteristics of Strain NR 7328

On Czapek-Yeast extract agar (CYA), the colonies grew rapidly and filled with Petri dishes after 7 days at 25° C., showing abundant conidiogenesis in the center of the dense floccose mycelium mat. The color of colonies was deep brown to dark brown (Munsell, 7.5YR2/2-7.5YR2/2). Mycelium was white. The color of reverse side was light yellow (Munsell, 2.5Y8/6). Exudate and soluble pigment were not produced.

On malt extract agar (MEA), colonies grew relatively slower than those on CYA at 25° C., attaining a diameter of 48–50 mm after 7 days at 25° C., forming plane, dense, heavily sporing colonies. The color of colonies was dark yellowish brown (Munsell, 10YR3/2). Mycelium was white but inconspicuous. The color of reverse side was pale yellow (Munsell, 5Y8/4). Exudate and soluble pigment were not observed.

On Czapek-Yeast extract agar with 20% sucrose (CY20S) at 25° C., the colonies grew rapidly similarly to those on CYA at 25° C. The color of colonies was also dark brown. Mycelium was white and floccose. The reverse color was yellowish white.

On CYA at 37° C., the colonies grew moderately to reach 17–18 mm in diameter in 7 days, which showed sulcate, umbonate colonies. Conidiogenesis was poor. The color of colonies was dark yellowish gray (Munsell, 5Y5/2). Reverse color was deep yellowish brown (Munsell, 5Y3/2).

On CYA at 5° C., germination was not observed.

Morphological Characteristics of Strain NR 7328

Conidial heads were radiate at first and split into several longitudinal columns. Strigmata was uniseriate, closely packed short phialides and covered almost entire of surface of vesicles. Vesicle was globose or nearly so, 35–55(–75) μm in diameter with heavy wall, colored in somewhat brown shade. Stipe was thick, smooth walled, 7.5–20×250–700(–1000) μm. Conidia was globose to subglobose, occasionally elliptical, pigmented in dark, 3.5–5.0 μm in diameter. Surface of the conidia was echinulate with widely spaced spines.

The strain NR 7328 formed dark colored in some shade of black, dense colonies with abundant conidiogenesis. Vesicle was globose or nearly so. Strigmata was in a single series. Conidia was globose to elliptical, echinulate, dark colored. On the basis of these distinctive characteristics, the present strain NR 7328 was identified as a strain of *Aspergillus japonicus*, designated as *Aspergillus japonicus* NR 7328 (DSM 10677).

Cultural Characteristics of Strains NR 7329, NR 7330, NR 7331, NR 7332 and NR 7334

On CYA, the colonies of these strains grew rapidly attaining to 53–61 mm in a diameter, except NR 7334 that were later than other strains, reached to 44–45 mm after 7 days at 25° C. All the colonies showed plane, veltinous texture with abundant, fructuous conidiogenesis. The color of colonies was dull bluish green (Munsell, 7.5BG4/4) or deep to soft blue green (Munsell, 5BG4/2-7/4). Mycelium was white only at margins and sometimes inconspicuous. The reverse color of NR 7329 was colonial yellow (Munsell, 5Y7/6) and that of the other strains was Naples yellow (Munsell, 2.5Y8/6) to soft yellow green (Munsell, 2.5GY7/2). Exudate and soluble pigment were not produced.

On MEA, the colonies grew rapidly, attaining 52–63 mm in diameter after 7 days at 25° C., plane, dense occasionally felty colonies showing looser texture than those on CYA at 25° C. The color of colonies was dull green to greenish gray (Munsell, 5G5/4-7/2). Mycelium was inconspicuous. The color of reverse side was colorless or dull yellow green (Munsell, 7.5GY6/4). Exudate and soluble pigment were not observed.

On CY20S at 25° C., The colonies grew rapidly to reach to 50–56 mm in diameter in 7 days, which showed dense, veltinous or felty colonies. The color and texture of the colonies were same as those on CYA at 25° C. Mycelium was white or light greenish yellow (Munsell, 10Y9/4) only at a margin. The reverse color of colonies was cream to medium greenish yellow (Munsell, 10Y7/6). Only the strain FE 6425 faintly produced reddish brown soluble pigment.

On CYA at 37° C., colonies grew rapidly and filled with Petri dish showing plane, powdery colonies. The color of colonies was grayish yellow green to sage green (Munsell, 7.5GY6/2-5GY6/2). The conidiogenesis was so profuse and the mycelium was inconspicuous or only at the margins. The reverse of the colonies was sulcate and colored buff to light reddish yellow (Munsell, 2.5Y6/6-7/6). Some of these colonies produced clear exudate.

On CYA at 5° C., germination was not observed for all of the strains.

Morphological Characteristics of Strains NR 7329, NR 7330, NR 7331, NR 7332 and NR 7334

Conidial heads were columnar. Strigmata was uniseriate with closely packed phialides which were paralleled to each other and the stipe axis. Phialides covered upper half to two-third of the vesicles. Vesicle was spatulate or funnel shaped with thick wall, 13–30 μm in width. Stipe was uncolored, smooth walled, gradually expanding into the vesicle up to 400 μm occasionally 500 μm in length. Conidia was globose or subglobose to ellipsoidal, 2.5–4.0 μm in diameter. Surface was various, smooth to rough and occasionally echinulated.

Colonies grew rapidly at 25° C. also at 37° C., colored in some dull green shade, dense, abundant conidiogenesis. Conidial head formed columnar. Vesicle was spatulated, fertile over the upper of half to two-third of that, with closely packed phialides to be parallel to each other and the axis. Strigmata was in a single series. Conidia was small, globose to ellipsoidal. On the basis of these distinctive characteristics, the present strains NR 7329, NR 7330, NR 7331, NR 7332 and NR 7334 were identified as a strain of *Aspergillus fumigatus* designated as *Aspergillus fumigatus* NR 7329 (DSM 10678), NR 7330 (DSM 10679), NR 7331 (DSM 10680), NR 7332 (DSM 10681) and NR 7334 (DSM 10682), respectively.

Compounds A and B of the present invention can be made by cultivating a microorganism belonging to the genus Aspergillus capable of making Compounds A and/or B under aerobic conditions in a culture medium and isolating Compounds A and B from the culture.

The cultivation in accordance with the present invention can be carried out in a culture medium which contains customary nutrients usable by the microorganism being cultivated. As carbon sources there can be mentioned, for example, glucose, sucrose, starch, glycerol, molasses, dextrin and mixtures thereof. Nitrogen sources are for example, soybean meal, cottonseed meal, meat extract, peptone, dried yeast, yeast extract, corn steep liquor, ammonium sulfate, sodium nitrate and mixtures thereof. Moreover, there may be added to the culture medium other organic or inorganic substances for promoting the growth of the microorganism and for increasing the production of Fungarrestins. Examples of such substances are inorganic salts such as, calcium carbonate, sodium chloride, phosphates and the like.

The cultivation is carried out under aerobic conditions in an aqueous medium preferably by submerged fermentation. The cultivation is suitably carried out at a temperature of 20° C.–37° C., with an optimal temperature of 27° C. The cultivation is preferably carried out at a pH 3 to 9. The cultivation time depends on the conditions under which the cultivation is carried out. In general, it is sufficient to proceed with the cultivation for 20–200 hours.

For isolation of Compounds A and B from the cultures, separation methods which are usually employed to isolate metabolites produced by microbes from their cultures can be used. For example, the mycelium can be separated from the fermentation broth by centrifugation or filtration and the objective compounds can be extracted from the filtrate with a water-immiscible organic solvent such as alkanol for example, n-butanol and esters for example, ethyl acetate, butyl acetate etc. On the other hand, the objective compounds contained in the separated mycelium can be obtained, for example, by extracting the mycelium with a solvent such as aqueous acetone or aqueous methanol, removing the solvent and further extracting the residue with a water-immiscible organic solvent. The thus obtained solvent layer is dried over a dehydrating agent such as sodium sulfate etc. and then concentrated under reduced pressure. The resulting crude Compounds A and B can be purified by means of partition methods, column chromatographical methods (using silica gel, aluminum oxide, octadecyl-silica gel, Sephadex LH-20 etc. as adsorbents) and High Performance Liquid Chromatography (using silica gel, octadecyl-silica gel and phenyl-silica gel etc. as adsorbents).

Compounds A and B were isolated in free form, but if required, can be converted into physiologically usable salts (e.q. sodium salt, ammonium salt etc.) by conventional methods.

Compounds A and B can be converted into Compounds A-1 to A-10 and B-1 to B-6, respectively, according to Processes A to F described hereinafter.

Process A

Compounds of the formula (I) in which $R^1$ is lower alkyl, $R^2$ is hydrogen, X and Y are CO and Z is O; or $R^1$ is hydrogen, $R^2$ is lower alkyl, X and Y are CO and Z is O; or $R^1$ and $R^2$ are lower alkyl, X and Y are CO and Z is O can be produced by alkylating Compound A or B with alkyl halide or alkysulfate in the presence of a base such as potassium carbonate or silver oxide in an inert solvent such as acetone or N,N-dimethylformamide. The reaction temperature can vary in a wide range between about −50° C. and 150° C., preferably between about 0° C. and 100° C. The methylation can also be performed by treatment Compound A or B with diazomethane in a solvent such as chloroform or methanol. The reaction temperature can vary in a wide range between about −0° C. and 80° C., preferably between about 10° C . and 30° C.

Process B

Compounds of the formula (I) in which $R^1$ is acyl, $R^2$ is hydrogen, X and Y are CO and Z is O; or $R^1$ is hydrogen, $R^2$ is acyl, X and Y are CO and Z is O; or $R^1$ and $R^2$ are acyl, X and Y are CO and Z is O can be produced by acylating Compound A or B with a carboxylic acid in the presence of a coupling agent such as carbodiimide in an inert solvent such as acetonitrile or dioxane. The reaction temperature can vary in a wide range between about −50° C. and 100° C., preferably between about −20° C. and 50° C. The acylation can also be accomplished using a reactive derivative of the said carboxylic acid such as for example, an acid chloride or a mixed anhydride with another organic acid, for example, benzene sulfonic acid. The acylation is optionally performed in the presence of a base such as sodium bicarbonate, pyridine, triethylamine or N,N-dimethylaminopyridine in an inert solvent such as methylene chloride, chloroform, acetonitrile or N,N-dimethylformamide.

Process C

Compounds of the formula (I) in which $R^1$ is lower alkyl, $R^2$ is acyl, X and Y are CO and Z is O; or $R^1$ is acyl, $R^2$ is lower alkyl, X and Y are CO and Z is O can be produced by acylating compounds of the formula (I) in which $R^1$ is lower alkyl, $R^2$ is hydrogen, X and Y are CO and Z is O; or $R^1$ is hydrogen, $R^2$ is lower alkyl, X and Y are CO and Z is O (as prepared according to the process A) with a carboxylic acid in the presence of a coupling agent such as carbodiimide in an inert solvent such as acetonitrile or dioxane. The reaction temperature can vary in a wide range between about −50° C. and 100° C., preferably between about −20° C. and 50° C. The acylation can also be carried out using a reactive derivative of the said carboxylic acid such as for example, an acid chloride or a mixed anhydride with another organic acid, for example, benzene sulfonic acid. The acylation is optionally performed in the presence of a base such as sodium bicarbonate, pyridine, triethylamine or N,N- dimethylaminopyridine in an inert solvent such as methylene chloride, chloroform, acetonitrile or N,N-dimethylformamide, or can be produced by alkylating compounds of the formula (I) in which $R^1$ is acyl, $R^2$ is hydrogen, X and Y are CO and Z is O; or $R^1$ is hydrogen, $R^2$ is acyl, X and Y are CO and Z is O (as prepared according to the above process B) with an alkyl halide or alkysulfate in the presence of a base such as potassium carbonate or silver oxide in an inert solvent such as acetone or N,N-dimethylformamide. The reaction temperature can vary in a wide range between about −50° C. and 100° C., preferably between about −20° C. and 50° C. The methylation can also be performed by treating compounds A or B with diazomethane in a solvent such as chloroform or methanol. The reaction temperature can vary in a wide range between about −0° C. and 80° C., preferably between about 10° C. and 30° C.

Process D

Compounds of the formula (I) in which X is CHOH, $R^1$ and $R^2$ are each hydrogen, lower alkyl or acyl, Y is CO and Z is O can be produced by reducing Compound A or B or the compound prepared according to the method described in the above process A, B or C by hydrogenation over a catalyst such as palladium on charcoal or platinum in an appropriate organic solvent such as ethyl alcohol or acetic acid, optionally, under elevated pressure; or by treatment with sodium borohydride in an appropriate organic solvent such as ethyl alcohol. The reaction temperature can vary in a wide range between about −80° C. and 50° C., preferably between about 0° C. and 30° C.

Process E

Compounds represented by the formula (I) in which Y is $CH_2$, $R^1$ and $R^2$ are each hydrogen, lower alkyl or acyl, X is CO or CHOH and Z is O can be produced by reducing Compound A or B, or the compound prepared according to the method described in the above process A, B, C or D by treatment with sodium borohydride in an appropriate organic solvent such as ethyl alcohol. The reaction temperature can vary in a wide range between about −80° C. and 50° C., preferably between about 0° C. and 30° C.

Process F

Compounds represented by the formula (I) in which Z is NH, and $R^1$ and $R^2$, X are each hydrogen, lower alkyl or acyl, X is CO or CHOH, and Y is CO or $CH_2$ can be produced by treatment of Compound A or B, or the compound prepared according to the method described in the above process A, B, C, D or E with ammonia in an appropriate organic solvent such as N,N-dimethylformamide at the temperature between about −40° C. and 80° C., preferably between about 0° C. and 30° C., followed by heating in an appropriate solvent such as toluene and benzene in the presence of weak acid such as pyridinium p-toluenesulfonate at the temperature between about 40° C. and 200° C., preferably between about 80° C. and 150° C.

Anti-proliferative Activity of Compounds of Formula I on Several Transformed Cell Lines The colo-rectum carcinoma cell line (HT-29 and SW480), the lung carcinoma cell line (H460a), the osteosarcoma cell line (Saos-2) and the pancreatic cell line (ASPC-1) were all purchased from ATCC (American type Cell Culture Collection) and were grown in culture in medium as recommended by ATCC. Anti-proliferative activities of the compounds on the breast carcinoma cell line (T-47D and MCF-7), the colo-rectum carcinoma cell line (COLO-320 DM and HCT116) and the lung carcinoma cell line (H1299) were also tested. For analysis of the effect of various compounds on growth of these cells, the cells were plated at a concentration that allowed for a minimum of four doublings at the end of the assay. The compounds to be analyzed were dissolved in 100% DMSO to yield a 10 mM stock solution. Each compound was diluted in $H_2O$ to 1 mM and was added to triplicate wells in the first row of a 96 well master plate which contains medium to yield a final concentration of 40 $\mu$M. The compounds were then serially diluted in medium in the "master plate". The diluted compound(s) were then transferred to test plates containing cells. The final concentration of DMSO in each well was 0.1% DMSO. MTT assays were done at different times after the addition of compounds. MTT (3-(4-5 methyl thiazole-2-yl)-2,5-diphenyl tetrazolium bromide, thiazolyl blue) was added to each well to yield a final concentration of 1 mg/ml. The plate was then incubated at 37° C. for 2.5–3 hours. The MTT containing medium was then removed and 50 $\mu$l of 100% ethanol was added to each well to dissolve the formazan. The absorbencies were then read using an automated plate reader (Bio-tek microplate reader). In case of Saos-2 cells, cells were plated in 6 well plates, compound added at different concentrations 24 hours after plating and then the cells were counted at different days after drug addition. The results are shown in Table 1.

TABLE 1

| | IC50($\mu$M) | |
|---|---|---|
| | Compound A | Compound B |
| Cell lines | | |
| Breast | | |
| T-47D | 5.8 | |
| MCF-7 | 1.5 | |
| Colo-rectum | | |
| HT29 | 5.8 | 4.8 |
| COLO-320 DM | 2.6 | |
| SW480 | 3~10 | |
| HCT116 | 1.3 | |
| Lung | | |
| H1299 | 3~4 | |
| H460A | 2.3 | 2.2 |
| Osteosarcoma | | |
| SAOS-2 | 0.3~1 | |
| Pancreatic | | |
| ASPC-1 | 6.2 | |

As shown in the above Table 1, Compounds A and B have inhibitory activity on proliferation of transformed cell lines. Therefore, compounds of formula I provided by the present invention are useful as an antitumor agent against breast cancer, colo-rectum cancer, lung cancer, osteosarcoma cancer and the like for appropriate administration to a mammal, both human and non-human.

Acute toxicity of compounds of formula I provided by the present invention were not observed.

The products in accordance with the invention can be used as medicaments, for example, in the form of pharmacuetical preparations for enteral (oral) administration. The products in accordance with the invention can be administered, for example, perorally, such as in the form of tablets, coated tablets, dragees, hard and soft gelatin capsules, solutions, emulsions or suspensions, or rectally, such as in the form of suppositories.

For therapeutic use, compounds of formula I and physiologically usable salts thereof can be prepared into pharmaceutical compositions of various forms. Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral or parenteral dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipiated aluminum hydroxide-calcium carbonate, dicalcium phosphate or lactose; disintegrating agents, such as maize starch; and lubricating agents, such as talc, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also orangic carrier materials. Thus, for tablets, coated tablets, dragees and hard gelatin capsules there can be used, for example, lactose, maize starch or derivatives thereof, talc, stearic acid or its salts. Suitable carriers for soft gelatin capsules are, for example, vegetable oils, waxes, fats and semi-solid and liquid polyols (depending on the nature of the active substance; no carriers are, however, required in the case of soft gelatin capsules). Suitable carrier materials for the preparation of solutions and syrups are, for example, water, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual perservatives, solubilizers, stabilizers, wetting agents, emulsifiers, sweeteners, colorants, flavorants, salts for varying osmotic pressure, buffers, coating agents and antioxidants.

The compounds of formula I or their salts can preferably be used for parenteral administration, and for this purpose are preferably made into preparations as lyophilisates or dry powders for dilution with customary agents, such as water or isotonic common salt solution.

For example Compound A can be administrated intravenously, subcutaneously or intramuscularly, conveniently in physiological saline, usually at a dose of 1 to 50 mg/kg/day, preferably 1 to 20 mg/kg/day; or in capsules or sugar-coated tablets and administrated at a dose of usually 1 to 100 mg/kg/day, preferably 5 to 50 mg/kg/day.

The following examples describe the present invention in more detail, but are not intended to limit the invention thereto. Unless otherwise specified, % means weight/volume %.

EXAMPLE 1

Flask Culture

A portion of the stock culture (0.1 ml) of *Aspergillus fumigatus* NR 7329 (DSM 10678) was inoculated into a 500-ml Erlenmeyer flask containing 100 ml of a medium consisting of 0.05% $Mg3(PO4)_2.8H_2O$, 0.8% KCl, 5.0% sucrose, 1.0% corn steep liquor, 2.0% Toast soya (Nisshin Seiyu Co. Ltd., Japan) and 0.03% Nissan disfoam CA-123 (Nippon Yushi Co. Ltd., Japan). The pH of the medium was adjusted to 6.5. The seed culture was incubated at 27° C. on a rotary shaker at 220 rpm for 3 days. Two ml of the aliquot were then transferred into hundred 500-ml flasks each containing 100 ml of the same medium as above. The fermentation was carried out on a rotary shaker under the same condition as the seed culture. After ca. 96 hours the yield of compounds reached a maximum. Then the whole broth was subjected to the isolation procedure described below.

Jar Fermentation

A portion of the stock culture (0.1 ml) of *Aspergillus fumigatus* NR 7329 (DSM 10678) was inoculated into a 500-ml Erlenmeyer flask containing 100 ml of the same medium as above. The first seed culture was incubated at 27° C. on a rotary shaker at 220 rpm. Two ml of the aliquot were then transferred into twenty-four 500-ml flasks each containing 100 ml of the same medium as above. The fermentation was conducted for 3 days under the same conditions. Six hundred ml each of resultant culture was inoculated into four 50-liter jar fermentors each containing 30 liters of the same medium containing, additionally, 500 ml of Nissan disfoam CA-123. The jar fermentation was carried out at 27° C. with agitation at 400 rpm and an air flow rate of 30 liters/minute. The maximum yield of compounds were reached after ca. 91 hours of fermentation, and the whole broth was subjected to the isolation procedures described below.

Isolation Procedure-I

The cultured broth (10 L) obtained in the above flask fermentation was separated into supernatant and mycelial cake by centrifugation. The supernatant (6.4 L) was extracted with ethyl acetate (6.4 L), and the organic layer was concentrated to dryness under reduced pressure. The concentrate (6.9 g) was dissolved in methanol (1 L) and partitioned with n-hexane (2 L), followed by removal of the n-hexane layer. The methanol layer was then concentrated to dryness under reduced pressure (crude extract I; 5.2 g). On the other hand, the mycelial cake was extracted with methanol (4.5 L), and the mixture was filtered to obtain a methanol extract. The methanol extract thus obtained was concentrated under reduced pressure, and the concentrate (1.5 L) was washed with n-hexane (1.5 L). The lower layer was concentrated to dryness under reduced pressure. The residue was dissolved in water (1.5 L) and the suspension thus obtained was extracted with ethyl acetate (1.5 L). The ethyl acetate layer was then concentrated to dryness under reduced pressure (crude extract II; 4.0 g) The crude extracts I and II were combined, and subjected to a column chromatography on YMC-GEL ODS-A 60-60/30 (50 g, YMC Co., LTD., Japan). The column was eluted with a mixture of water and methanol. The eluate containing active compounds were combined and concentrated to dryness under reduced pressure. The residue (7.1 g) was then subjected to a column chromatography on Sephadex LH-20 (4 L, Pharmacia, Sweden) using methanol as an eluent. The eluate containing active compounds were combined to obtain 2 fractions (fraction 1; 1.98 g, fraction 2; 63 mg). The fraction 1 was subjected to a preparative HPLC (CAPCELL PAK C18 UG-120A; Shiseido, Japan) using 30% aqueous acetonitrile as an eluent. Fractions containing Compound A and B, respectively were concentrated to dryness under reduced pressure. The residue containing Compound A (275 mg) was re-subjected to a preparative HPLC (YMC-Pack Ph A-414; YMC Co., Ltd., Japan) using 30% aqueous acetonitrile as an eluent. Fractions containing Compound A were concentrated to dryness under reduced pressure, followed by crystallization from methanol to obtain white crystals of Compound A (132 mg). The residue containing Compound B (115 mg) was treated in the same manner to obtain white crystals of Compound B (74 mg).

Isolation Procedure-II

The cultured broth (120 L) obtained in the above jar fermentation was separated into supernatant and mycelial cake by centrifugation. The supernatant (100 L) was extracted with ethyl acetate (72 L), and the organic layer was concentrated to dryness under reduced pressure. The concentrate (160 g) was dissolved in methanol (3 L) and partitioned with n-hexane (5 L), followed by removal of the n-hexane layer. The methanol layer was then concentrated to dryness under reduced pressure (crude extract I; 70 g). On the other hand, the mycelial cake was extracted with methanol (36 L), and the mixture was filtered to obtain a methanol extract. The methanol extract thus obtained was concentrated under reduced pressure, and the concentrate (3 L) was washed with n-hexane (3 L). The lower layer was concentrated to dryness under reduced pressure. The residue was dissolved in water (2 L) and the suspension thus obtained was extracted with ethyl acetate (2 L). The ethyl acetate layer was then concentrated to dryness under reduced pressure (crude extract II; 230 g). The crude extract I and II were combined and subjected to a column chromatography on silica gel (300 g, Wakogel C-200; Wako Pure Chemical Industries, Ltd., Japan). The column was eluted with a mixture of dichloromethane and methanol. The eluate containing active compounds was concentrated to dryness under reduced pressure. The residue (77 g) was then subjected to a column chromatography on Sephadex LH-20 (44 L) using methanol as an eluent. The eluate containing active compounds were combined to obtain 3 fractions (fraction 1, 2, 3). The fraction 1 (10.61 g) containing Compounds A and B was subjected to a Lobar column (LiChroprep Si60 size C; Merck, Germany) using dichloromethane and methanol as an eluent. The fractions containing Compound A were concentrated to dryness under reduced pressure, followed by crystallization from methanol to obtain white crystals of Compound A (2.39 g). The fractions containing Compound B were treated in the same manner to obtain Compound B (0.72 g) as white crystals.

EXAMPLE 2

*Aspergillus fumigatus* NR 7334 (DSM 10682) and *Aspergillus japonicus* NR 7328 (DSM 10677) were cultured in the same manner mentioned in Example 1.

The isolation yield of Compounds A and B are shown in Table 2.

TABLE 2

| Strain No. | Compound A | Compound B |
|---|---|---|
| NR 7328 | 1 mg/L | — |
| NR 7334 | 45 mg/L | 20 mg/L |

EXAMPLE 3

Flask Culture

A portion of the stock culture (0.1 ml) of *Aspergillus fumigatus* NR 7330 (DSM 10679) was inoculated into a 500-ml Erlenmeyer flask containing 100 ml of a medium consisting of 2% glucose, 1% potato starch, 1.5% glycerol, 1% Toast soya, 0.25% polypeptone, 0.35% yeast extract, 0.3% NaCl, 0.5% $CaCO_3$, 0.005% $ZnSO_4.7H_2O$, 0.0005% $CuSO_4.5H_2O$, 0.0005% $MnSO_4.4H_2O$, and 0.03% Nissan disfoam CA-123. The pH of the medium was not adjusted. The procedure and condition of the seed and production culture were same as flask culture 1. After around 96 hours of fermentation, the whole broth was subjected to the isolation procedure. *Aspergillus fumigatus* NR 7331 (DSM 10680) and *Aspergillus fumigatus* NR 7332 (DSM 10681) were cultured in the same manner mentioned above.

The isolation yield of Compounds A and B are shown in Table 3.

TABLE 3

| Strain No. | Compound A | Compound B |
|---|---|---|
| NR 7330 | 14 mg/L | 11 mg/L |
| NR 7331 | 2 mg/L | 4 mg/L |
| NR 7332 | 4 mg/L | 7 mg/L |

EXAMPLE 4

Preparation of Compounds A-1 and B-1

A solution of 21 mg of Compound A in 1.4 ml of pyridine/acetic anhydride (1:1, v/v) was stirred at room temperature for 1 hour. The mixture was dried under reduced pressure to yield 26 mg of Compound A-1 as a white powder.

A solution of 21 mg of Compound B in 1.4 ml of pyridine/acetic anhydride (1:1, v/v) was stirred at room temperature for 1 hour. The mixture was dried under reduced pressure to yield 26 mg of Compound B-1 as a white powder.

EXAMPLE 5

Preparation of Compounds A-4 and B-4

To a solution of 4 mg of Compound A in 3 ml of methanol was added excess diazomethane in ethyl ether at room temperature. Left for 8 hours, and the solution was evaporated in vacuo. The residue was purified by preparative TLC (Kieselgel 60 F254, Art. 5715 ; Merck, Germany) to yield 4 mg of Compound A-4 as a white powder.

A solution of 6 mg of Compound B in 3 ml of methanol was treated in the same manner to yield 5 mg of Compound B-4 as a white powder.

EXAMPLE 6

Preparation of Compound A-7

To a solution of 5 mg of Compound A-4 in 0.2 ml of dimethylsulfoxide there was added 0.2 ml of acetic anhydride at room temperature. The mixture was stirred for 17 hours, evaporated under reduced pressure and the residue purified by preparative HPLC to yield 0.5 mg of Compound A-7 as a white powder.

EXAMPLE 7

Preparation of Compound A-8

To a solution of 50 mg of Compound A in 10 ml of ethyl alcohol there were added 15 mg of palladium charcoal. The mixture was stirred under hydrogen atmosphere at room temperature for 15 hours. After removal of the catalyst, the solution was evaporated under reduced pressure. The residue was purified by HPLC (CAPCELL Pak C18 SG120A) using a mixture of phosphate buffer and acetonitrile as an eluent to yield 5 mg of Compound A-8 as a white powder.

EXAMPLE 8

Preparation of Compound A-9

To a solution of 20 mg of Compound A in 4 ml methanol there were added 2.6 mg of sodium borohydride at 0° C. under argon atmosphere. After stirring for 4 hours, the solution was evaporated under reduced pressure and 4 ml of ethyl acetate and 4 ml of distilled water were added to the residue. The solution was shaken, the organic layer evaporated under reduced pressure and the residue purified by HPLC (CAPCELL PAK $C_{18}$ SG120A) using a mixture of phosphate buffer and acetonitrile as an eluent to yield 15 mg of Compound A-8 and 2 mg of Compound A-9 as white powders.

EXAMPLE 9

Preparation of Compounds A-5, A-6, B-5 and B-6

To a solution of 3 mg of Compound A-4 in 0.2 ml of pyridine there was added 4.5 mg of (−)-α-methoxy-α-trifluoromethylphenylacetyl chloride. The mixture was stirred for 5 hours. After removal of pyridine under reduced pressure the residue was purified by preparative TLC (Kieselgel 60 $F_{254}$, Art. 5715) to yield 3 mg of Compound A-5 as a white powder.

To a solution of 3 mg of Compound A-4 in 0.2 ml of pyridine there was added 4.5 mg of (+)-α-methoxy-α-trifluoromethylphenylacetyl chloride. The mixture was stirred for 5 hours. After removal of pyridine under reduced pressure the residue was purified by preparative TLC (Kieselgel 60 $F_{254}$, Art. 5715) to yield 3 mg of Compound A-6 as a white powder.

To a solution of 2 mg of Compound B-4 in 0.2 ml of pyridine there was added 4.5 mg of (−)-α-methoxy-α-trifluoromethylphenylacetyl chloride. The mixture was stirred for 5 hours. After removal of pyridine under reduced pressure the residue was purified by preparative TLC (Kieselgel 60 $F_{254}$, Art. 5715) to yield 2 mg of Compound B-5 as a white powder.

To a solution of 2 mg of Compound B-4 in 0.2 ml of pyridine there was added 4.5 mg (+)-α-methoxy-α-trifluoromethylphenylacetyl chloride. The mixture was stirred for 5 hours. After removal of pyridine under reduced pressure the residue was purified by preparative TLC (Kieselgel 60 $F_{254}$, Art. 5715) to yield 2 mg of Compound B-6 as a white powder.

EXAMPLE 10

Preparation of Compounds A-3 and B-3

To a solution of 5 mg of Compound A in 0.8 ml of pyridine there were added 4 mg of p-bromobenzoyl chloride. The mixture was stirred for 1 hour. After removal of pyridine under reduced pressure the residue was purified by preparative TLC (Kieselgel 60 $F_{254}$, Art. 5715) to yield 2 mg of Compound A-2 and 0.5 mg of Compound A-3 as white powders.

A solution of 5 mg of Compound B in 0.8 ml of pyridine was treated in the same manner to yield 1 mg of Compound B-2 and 2 mg of Compound B-3 as white powders.

EXAMPLE 11

Preparation of Compounds A-2 and B-2

To a solution of 200 mg of Compound A in 20 ml of acetonitrile there were added 164 mg of p-bromobenzoyl chloride and 120 mg of potassium carbonate. The mixture was stirred for 30 min. at room temperature. The reaction mixture was diluted with ethyl acetate and washed with distilled water. The organic layer was dried over anhydrous sodium sulfate and evaporated under reduced pressure. The residue was chromatographed on silica gel (Wakogel C-200) using a mixture of ethyl acetate and hexane as an eluent to yield 100 mg of Compound A-2 as a white powder.

A solution of 200 mg of Compound B in 20 ml of acetonitrile was treated in the same manner to yield 200 mg of Compound B-2 as a white powder.

EXAMPLE 12

Preparation of Compounds A-10

To a solution of 72.9 mg of Compound A in 0.25 ml of dry DMF under argon there was added 0.5 ml of freshly prepared NH3 in DMF solution. After 30 min. volatiles were removed under reduced pressure. To the solid residue there were added 22 mL of toluene and 10 mg of pyridinium p-toluenesufonate. The mixture was refluxed for a total of 125 min., then cooled, and volatiles removed under reduced pressure. The product was purified by chromatography on silica gel, eluting with hexane-ethyl acetate (1:1) to give 45.9 mg of Compound A-10 as a white powder.

The following example illustrates an antitumor agent containing Compound A provided present invention:

EXAMPLE

Tablets containing the following ingredients were manufactured in a conventional manner:

| | |
|---|---|
| Compound A | 100 mg |
| Starch | 26 mg |
| Carboxymethylcellulose calcium | 15 mg |
| Crystalline cellulose | 20 mg |
| Magnesium stearate | 4 mg |
| | 165 mg |

We claim:
1. A compound of formula (I),

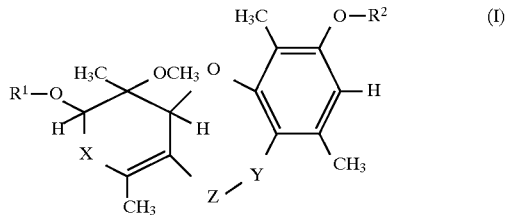

wherein
$R^1$ and $R^2$ are independently hydrogen, unsubstituted lower alkyl, lower alkyl substituted by lower alkoxy or lower alkyl thio, or acyl which is unsubstituted or substituted by one or more of lower alkyl, lower alkyl substituted by halogen or lower alkoxy;
X is CO or CHOH;
Y is CO or $CH_2$; and
Z is O, and epimers and enantiomers thereof, or the physiologically usable salts thereof.

2. The compound of claim 1, wherein X is CO.
3. The compound of claim 2, wherein Y is CO.
4. The compound of claim 3, wherein $R^1$ is hydrogen and $R^2$ is hydrogen.
5. The compound of claim 4, wherein the specific rotation of the compound is $[\alpha]^{23}_D=+272°$ (c=0.56, in methanol).
6. The compound of claim 4, wherein the specific rotation of the compound is $[a]^{23}_D=-8°$ (c=0.52, in methanol).

7. The compound of claim 2, wherein $R^1$ is acyl.
8. The compound of claim 7, wherein $R^1$ is acetyl.
9. The compound of claim 8, wherein $R^2$ is acyl.
10. The compound of claim 9, wherein $R^2$ is acetyl.
11. The compound of claim 7, wherein $R^1$ is p-bromobenzoyl.
12. The compound of claim 11, wherein $R^2$ is hydrogen.
13. The compound of claim 7, wherein $R^1$ is (−)-α-methoxy-α-(trifluoromethyl)phenylacetyl.
14. The compound of claim 13, wherein $R^2$ is lower alkyl.
15. The compound of claim 14, wherein $R^2$ is methyl.
16. The compound of claim 7, wherein $R^1$ is (+)-α-methoxy-α-(trifluoromethyl)phenylacetyl.
17. The compound of claim 16, wherein $R^2$ is lower alkyl.
18. The compound of claim 17, wherein $R^2$ is methyl.
19. The compound of claim 2, wherein $R^1$ is substituted lower alkyl.
20. The compound of claim 19, wherein $R^1$ is methylthiomethyl.
21. The compound of claim 20, wherein $R^2$ is lower alkyl.
22. The compound of claim 21, wherein $R^2$ is methyl.
23. The compound of claim 2, wherein $R^1$ is hydrogen.
24. The compound of claim 23, wherein $R^2$ is acyl.
25. The compound of claim 24, wherein $R^2$ is p-bromobenzoyl.
26. The compound of claim 23, wherein $R^2$ is lower alkyl.
27. The compound of claim 26, wherein $R^2$ is methyl.
28. A pharmaceutical composition comprising a therapeutically effective amount of a compound of formula I

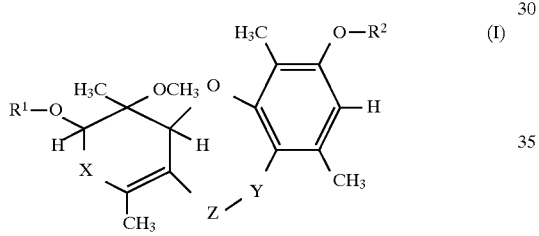

wherein
  $R^1$ and $R^2$ are independently hydrogen, unsubstituted lower alkyl, lower alkyl substituted by lower alkoxy or lower alkyl thio, or acyl which is unsubstituted or substituted by one or more of lower alkyl, lower alkyl substituted by halogen and lower alkoxy;
  X is CO or CHOH;
  Y is CO or $CH_2$; and
  Z is O, and epimers and enantiomers thereof,
or the physiologically usable salts thereof, and a pharmaceutically acceptable carrier.

29. A method of treating breast cancer, colo-rectum cancer, lung cancer, and osteosarcoma cancer in a host in need of such treatment comprising administering to the host a therapeutically effective amount of a compound of formula I

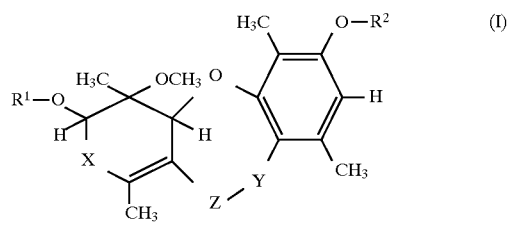

wherein
  $R^1$ and $R^2$ are independently hydrogen, unsubstituted lower alkyl, lower alkyl substituted by lower alkoxy or lower alkyl thio, or acyl which is unsubstituted or substituted by one or more of lower alkyl, lower alkyl substituted by halogen, and lower alkoxy;
  X is CO or CHOH;
  Y is CO or $CH_2$; and
  Z is O, and epimers and enantiomers thereof,
or the physiologically usable salts thereof, and a pharmaceutically acceptable carrier.

* * * * *